United States Patent
Cunningham et al.

(10) Patent No.: US 7,981,138 B2
(45) Date of Patent: Jul. 19, 2011

(54) SURGICAL SUTURE NEEDLE

(75) Inventors: Scott Cunningham, Cheshire, CT (US);
William Powers, Cheshire, CT (US);
Anibal Rodrigues, Bridgeport, CT (US)

(73) Assignee: Tyco Healthcare Group LP, Norwalk, CT (US)

(*) Notice: Subject to any disclaimer, the term of this patent is extended or adjusted under 35 U.S.C. 154(b) by 0 days.

(21) Appl. No.: 12/643,053

(22) Filed: Dec. 21, 2009

(65) Prior Publication Data
US 2010/0094336 A1 Apr. 15, 2010

Related U.S. Application Data

(63) Continuation of application No. 10/618,994, filed on Jul. 14, 2003, now Pat. No. 7,655,024.

(51) Int. Cl.
*A61B 17/06* (2006.01)

(52) U.S. Cl. ........................................ 606/222; 606/223

(58) Field of Classification Search .......... 606/222–223, 606/184–185; 604/273; 128/339
See application file for complete search history.

(56) References Cited

U.S. PATENT DOCUMENTS

| | | | |
|---|---|---|---|
| 20,409 A | 6/1858 | Jas | |
| 461,602 A | 10/1891 | Boult | |
| 527,263 A | 10/1894 | Blanchard | |
| 1,599,059 A | 9/1926 | Morton | |
| 3,038,475 A | 6/1962 | Orcutt | |
| 3,094,123 A | 6/1963 | Kurtz | |
| 3,238,942 A | 3/1966 | Lincoff | |
| 3,840,015 A | 10/1974 | Gain | |
| 4,133,339 A | 1/1979 | Naslund | |
| 4,237,892 A | 12/1980 | Ritter et al. | |
| 4,513,747 A | 4/1985 | Smith | |
| 4,524,771 A | 6/1985 | McGregor et al. | |
| 4,660,559 A | 4/1987 | McGregor et al. | |
| 4,799,483 A | 1/1989 | Kraff | |
| 4,799,484 A | 1/1989 | Smith et al. | |
| 4,932,961 A | 6/1990 | Wong et al. | |
| 5,002,564 A * | 3/1991 | McGregor et al. | 606/223 |
| 5,002,565 A | 3/1991 | McGregor | |
| 5,030,228 A | 7/1991 | Wong et al. | |
| 5,064,411 A | 11/1991 | Gordon | |
| 5,100,431 A | 3/1992 | Buster et al. | |

(Continued)

FOREIGN PATENT DOCUMENTS

DE    3712163 A1    10/1988

(Continued)

OTHER PUBLICATIONS

European Search Report for EP 03764656.9-2310 date of completion is Feb. 22, 2010, (3 pages).

*Primary Examiner* — Gary Jackson
*Assistant Examiner* — Diane Yabut

(57) ABSTRACT

A surgical needle is disclosed and includes an elongated needle body defining a longitudinal axis The surgical needle has a first end for attachment to a suture and a second needled end for penetrating tissue. The needled end includes lower and upper opposed surfaces and a pair of side surfaces extending between the lower and upper surfaces and being contiguous therewith. The upper surface and side surfaces extend to a pointed tip. The lower surface extends to a cutting edge, which is defined at the intersection of the side surfaces and proximal of the pointed tip. The cutting edge extends in oblique relation relative to the longitudinal axis and terminates at the pointed tip.

19 Claims, 4 Drawing Sheets

U.S. PATENT DOCUMENTS

| | | | |
|---|---|---|---|
| 5,178,628 A | 1/1993 | Otsuka et al. |
| 5,330,441 A | 7/1994 | Prasad et al. |
| 5,342,397 A | 8/1994 | Guido et al. |
| 5,476,480 A | 12/1995 | Matsutani et al. |
| 5,665,078 A | 9/1997 | McGregor et al. |
| 5,730,732 A | 3/1998 | Sardelis et al. |
| 5,749,897 A | 5/1998 | Matsutani et al. |
| 5,762,811 A | 6/1998 | Munoz |
| 5,776,268 A | 7/1998 | McJames et al. |
| 5,797,961 A | 8/1998 | Smith |
| 5,891,164 A | 4/1999 | Dabir et al. |
| 6,009,933 A | 1/2000 | Doyle et al. |
| 6,018,860 A | 2/2000 | Smith et al. |
| 6,322,581 B1 | 11/2001 | Fukuda et al. |
| 2004/0106948 A1 | 6/2004 | Cunningham |

FOREIGN PATENT DOCUMENTS

| | | |
|---|---|---|
| GB | 915820 A | 1/1963 |
| JP | 63038441 A | 2/1988 |
| SU | 1428360 A1 | 10/1988 |

\* cited by examiner

SURGICAL SUTURE NEEDLE

CROSS-REFERENCE TO RELATED APPLICATION

This application is a continuation of and claims the benefits of and priority to U.S. patent application Ser. No. 10/618,994, which was filed on Jul. 14, 2003, now U.S. Pat. No. 7,655,024. The entire contents of which are incorporated herein by reference.

BACKGROUND

1. Technical Field

The present disclosure relates to a surgical suturing needle for suturing cutaneous and subcutaneous tissue, and in particular, relates to a surgical needle having a multifaceted penetrating needle end characterized by enhanced penetrability and needle hardness.

2. Background of Related Art

Suturing needles for applying sutures, or stitches, by hand in cutaneous and subcutaneous tissue are well known in the art. Typically, the suturing needles are used to close wounds or adjoin adjacent tissue, often at the conclusion of a surgical procedure. Suturing needles are usually made from a cut blank of material such as stainless steel. The cut blank is metal-worked using well known machining techniques to form the suturing needle. The needle generally includes a shaft, a rear end portion with an aperture or channel to secure a suture thread and a needle head at a front end portion for puncturing skin and passing through tissue. The needle head typically incorporates a sharpened needle tip at its distal end and cutting edges. Alternatively, the needle tip may be of a tapered configuration. Straight and curved needles including multiple curved configurations are also known in the art.

An important consideration in the design of surgical suturing needles is needle sharpness. Sharper needles require less force to penetrate tissue and thus cause less tissue trauma. In addition, a sharper needle reduces fatigue on the needle itself, making it less likely to bend or break during suturing. Needle sharpness is typically defined in terms of "penetration force"—the force necessary for a needle to puncture, or penetrate, the tissue. The penetration force is primarily determined by the design and sharpness of the needle point and the cutting edges formed on the needle head. Needle sharpness is also affected by drag force on the needle as it travels through the tissue. The drag force also depends upon the design and sharpness of the needle, and the presence of a lubricating coating.

Another important consideration in needle design and manufacture is to maximize resistance to bending or breakage during use. The strength of a suturing needle is a measure of its ability to resist bending and is determined by such factors as (a) the material of fabrication, (b) the cross-sectional shape of the needle, and (c) the heat treatment applied to the needle during manufacturing. Needle strength should be balanced by needle ductility, which is defined in terms of the ability of the needle to be reshaped after it flexes from its original shape. A surgical needle with good strength characteristics but little or no ductility can be brittle, and may snap and break during use. It is generally known that in working with a metallic material, as the strength of the material increases the ductility will decrease. Therefore, it is desirable to carefully balance the strength and ductility characteristics of a suturing needle.

SUMMARY

Accordingly, the present disclosure is directed to further advancements in surgical suturing needles. The surgical needle of the present disclosure possesses enhanced needle attributes including needle sharpness and resistance to bending or breaking during use. In one embodiment, the surgical needle includes an elongated needle body defining a longitudinal y axis and x and z axes transverse to the y axis. The elongated needle body includes a central shaft, a first end for attachment to a suture and a second needled end for penetrating tissue. The needled end includes lower and upper opposed, preferably, planar surfaces and a pair of side surfaces extending between the lower and upper surfaces and contiguous therewith. The upper surface and side surfaces extend to a pointed tip. The lower surface extends to a cutting edge defined at the intersection of the side surfaces and proximal of the pointed tip. The cutting edge extends in oblique relation relative to the longitudinal axis of the needle body and terminates at the pointed tip. The linear cutting edge intersects the upper surface at an angle ranging from about 15° to about 30° relative to the longitudinal axis.

In the preferred embodiment, the needle end defines a first transverse cross-sectional dimension adjacent the central shaft, and having a general trapezoidal configuration. The needle end also defines a second transverse cross-sectional dimension adjacent the pointed tip, and having a general triangular configuration. The first cross-sectional dimension may define a dimension along the z-axes corresponding to a first width of the needle end with the first width being at least equal to, preferably, greater than, a corresponding shaft width of the central shaft. The first cross-sectional dimension defines a dimension along the x-axis corresponding to a first height of the needle end with the first height being less than a corresponding shaft height of the central shaft.

The needle body may be curved along the longitudinal axis, preferably, defining an angle of curvature ranging from about 80° to about 180°. Alternatively, the needle body may be straight.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure.

BRIEF DESCRIPTION OF PREFERRED EMBODIMENTS

Figure 1:
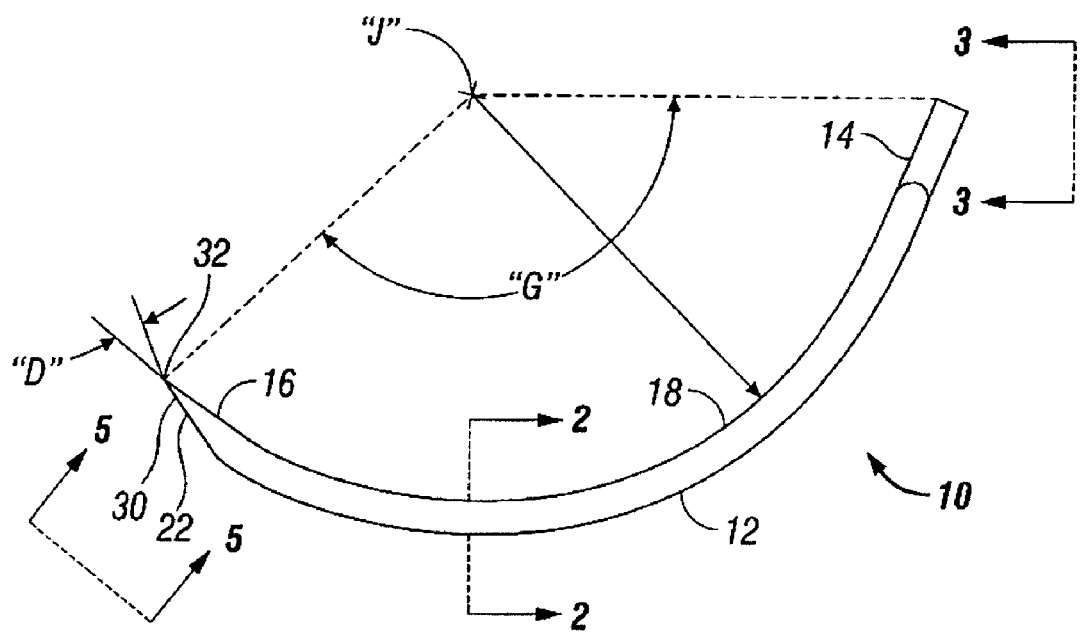
FIG. 1 is a side elevational view of the surgical needle in accordance with the principles of the present disclosure.

Preferred embodiment(s) of the surgical needle of the present disclosure will now be described in detail with reference to the drawings wherein like reference numerals identify similar or like elements throughout the several views. As used herein, the term "distal" refers to that portion which is further from the user, while the term "proximal" refers to that portion which is closest to the user.

Figure 2:
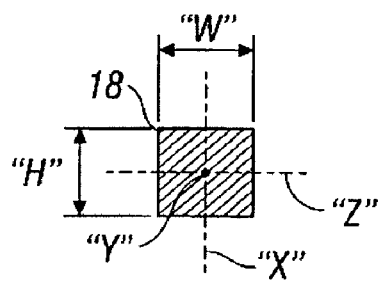
FIG. 2 is a cross-sectional view of the central shaft of the surgical needle taken along the lines 2-2 of FIG. 1.

With reference now to FIG. 1, the surgical needle 10 of the present disclosure is illustrated. Surgical needle 10 includes elongated needle body 12 having first or proximal end 14 and second or distal needled end 16. Needle body 12 is curved along its length through an arc "G" ranging from about 90° to about 180°. Other angles of curvature are also envisioned. It is also contemplated that needle body 12 may be straight. As depicted in FIG. 2, needle body 12 defines longitudinal axis "y" which extends along the length of needle body 12 and transverse axes "x" and "z". Transverse axes "x" and "z" correspond to the height and width dimensions of needle body 12, respectively.

With continued reference to FIGS. 1 and 2, needle body 12 defines central shaft 18 which is preferably rectangular in cross-section defining a height "H" (corresponding to an x-dimension) and a width "W" (corresponding to a z-dimension) as best depicted in FIG. 2. The ratio of the dimensions of the height "H" to width "W", i.e., "H"/"W" is preferably less than 1.1/1, preferably about 1.06/1 although other ratios are also contemplated. Although a greater "H"/"W" ratio (i.e., a more pronounced rectangular cross-section) may increase the strength of central shaft 18, the reduced ratio of 1.1/1 or less is more desirable. Specifically, the cross-section of central shaft 18 is easier to handle by the surgeon and may be more easily manipulated by a needle holder, e.g., needle forceps. Central shaft 18 may also be square in cross-section or alternatively rounded.

Figure 3:
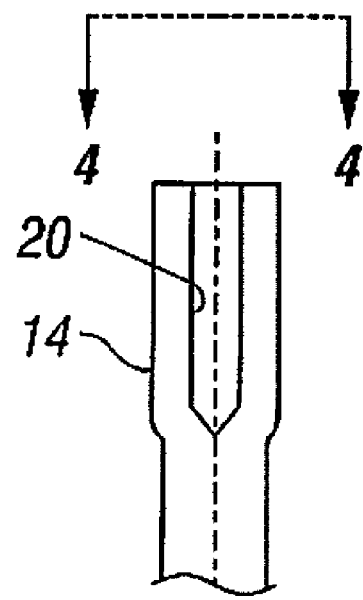
FIG. 3 is an enlarged plan view of the suture end of the surgical needle taken along the lines 3-3 of FIG. 1.
Figure 4:
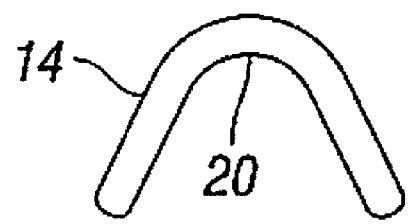
FIG. 4 is an axial view of the suture end of the surgical needle taken along the lines 4-4 of FIG. 3.

With reference now to FIGS. 3 and 4, in conjunction with FIG. 1, first end 14 defines an open U-shaped channel 20 dimensioned for reception of a suture end of a suture. U-shaped channel 20 is closed about the suture end through conventional swaging or crimping processes to secure the suture to elongated needle body 12. The dimensioning of U-shaped channel 20 of first end 14 may be selected to provide for permanent (non-detachable) or detachable securement of the suture to needle body 12. The type of securement effectuated is also dependent upon the swaging force employed during the attachment process. It is further envisioned that first end 14 may be provided with an enclosed bore or aperture formed through, e.g., a laser drilling process, for reception of the suture end. Adhesive suture attachment methodologies are also envisioned.

Figure 5:
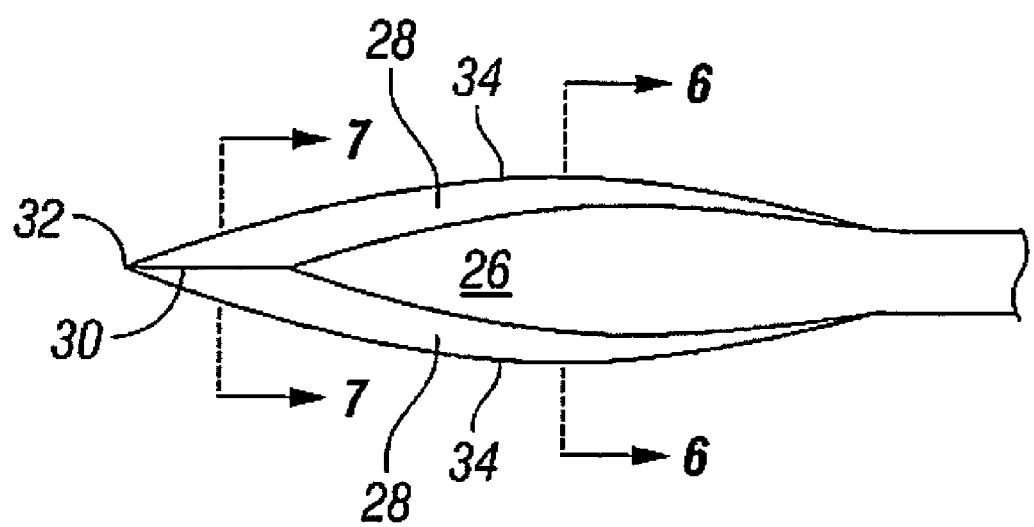
FIG. 5 is a top plan view of the penetrating needle end of the surgical needle taken along the lines 5-5 of FIG. 1.
Figure 6:
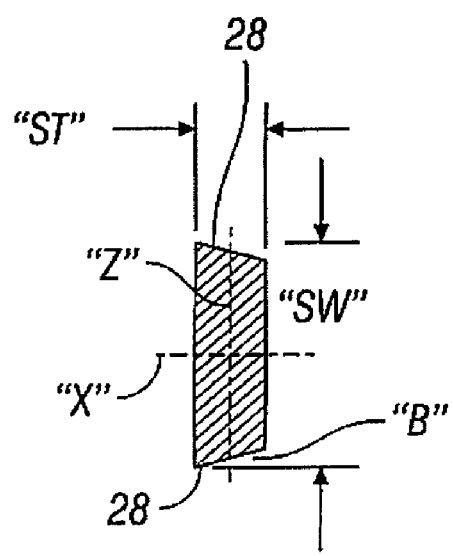
FIG. 6 is a cross-sectional view of the needle end taken along the lines 6-6 of FIG. 5.
Figure 7:
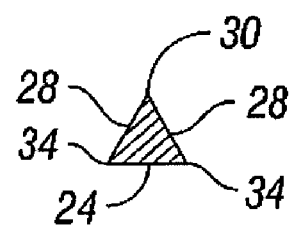
FIG. 7 is a cross-sectional view of the needle end taken along the lines 7-7 of FIG. 5.

Referring now to FIGS. 5-7, in view of FIG. 1, needled end 16 will be discussed in detail. Needled end 16 includes enlarged needle head 22 which is advantageously dimensioned to reduce the penetration force required to penetrate tissue while optimizing needle strength. Specifically, needle head 22 includes first and second surfaces 24, 26 (which will be referred to hereinafter as upper and lower surfaces 24, 26 for descriptive purposes) and side surfaces 28 which interconnect the upper and lower surfaces 24, 26. Side surfaces 28 intersect at linear cutting edge 30 which terminates at needle point 32. Upper and lower surfaces 24, 26 are preferably planar and in substantial parallel relation to the each other. Upper surface 24 extends to, and is coterminous with, needle point 32 while lower surface 26 terminates at the beginning of cutting edge 30. Side surfaces 28 commence at central shaft 18 and extend to intersect along cutting edge 30. The dimension or width of each side surfaces 28 decreases from needle point 32 to gradually transition into central shaft 18 of needle body 12.

As appreciated, by virtue of the configuration of needle head 22, three primary cutting edges for penetrating tissue are provided. Two primary cutting edges 34 are defined along the intersection of side surfaces 28 and upper surface 24, and the remaining primary cutting edge is the linear cutting edge 30 defined at the juncture of the two side surfaces 28.

As depicted in FIGS. 6 and 7, needle head 22 provides a multiple cross-sectional configuration. The cross-section along a first intermediate portion of needle head 22 (FIG. 6) defines a general narrowed trapezoidal configuration. The height "ST" at this location is preferably no greater than about 50% (or one-half) of the corresponding height "H" of central shaft 18, most preferably, no greater than about 45% of the height "H". The maximum width "SW" at this location is no less than 1.0 times the corresponding width "W" of central shaft 18. In one preferred embodiment, the maximum width "SW" is no less than 1.5 times the width "W" of the central shaft 18. Accordingly, needle head 22 at this location provides a reduced profile or cross-sectional dimension which significantly facilitates passage of the needle head 22 through tissue. In addition, the pronounced height to width ("H"/"W") ratio substantially increases the overall strength of needle head 22. The included angle "B" defined at the intersection of side surfaces 28 and upper surface 24 is sufficiently large to avoid the potential of needle breakage at this location. The preferred angle "B" ranges from about 35° to about 55°.

The cross-sectional configuration of needle head 22 adjacent needle point 32 is triangular having the three cutting edges 30, 34 in general close proximity to define a narrowed sharp needle end to facilitate penetration through the tissue. The preferred included angle "d" (FIG. 1) defined at the intersection of linear cutting edge 30 and upper surface 24 is preferably between about 15° and about 30°.

The surgical suturing needle of the present disclosure possesses attributes of primary significance in suturing needles. Specifically, by virtue of the multiple cross-sectional character of needle 10, the needle possesses superior needle sharpness and also demonstrates superior strength. In particular, the narrowed triangular cross-sectional dimension of the needle head 22 adjacent the needle point 32 with its closely positioned cutting edges 30, 34 produces a sharpened profile which significantly reduces the penetration force required to penetrate the body tissue. Moreover, the cutting edges 34 extend to the widest part of needle head 22 thereby slicing, in conjunction with linear cutting edge 30, the tissue as it passes through and providing an opening which is slightly larger than the cross-section of central shaft 18, consequently, significantly reducing the drag force and permitting the shaft 18 to easily pass through the tissue. The flattened trapezoidal cross-section of the needle head 22 also produces a profile conducive to continued passage of the needle head 22 through the tissue.

The choice of materials of surgical needle 10 is made to optimize strength, ductility and resistance to bending or breaking of the needle. However, as noted, the cross-sectional shape and dimensions of the needle contributes significantly to the physical characteristics of the needle. Preferred materials include stainless steel such as series "300" stainless steels, which typically have tensile strengths of between 325,000-350,000 lbs/in.sup.2, attain their high strength from undergoing cold working as the material is converted from an ingot to wire of the desired diameter.

Surgical needle 10 is manufactured through conventional cutting, coining, grinding and/or swaging processes, and may be heat treated to further enhance its strength and resistance to bending.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical needle, which comprises:
an elongated needle body defining a longitudinal y axis and x and z axes transverse to the y axis, the elongated needle body including a central shaft and having a first end for attachment to a suture and a second needle end for penetrating tissue, the second needle end having a transition area, a proximal portion of the second needle end disposed proximally of the transition area including a first length having a trapezoidal transverse cross-section and a distal portion of the second needle end disposed distally of the transition area including a second length having a triangular transverse cross-section, the first length being longer than the second length.

2. The surgical needle according to claim 1 wherein the trapezoidal cross-sectional dimension defines a dimension along the z-axes corresponding to a first width of the second needle end, the first width at least equal to a corresponding shaft width of the central shaft.

3. The surgical needle according to claim 2 wherein the first width is greater than a corresponding shaft width of the central shaft.

4. The surgical needle according to claim 3 wherein the first width is not less than about 1.5 times the shaft width.

5. The surgical needle according to claim 1 wherein the trapezoidal cross-sectional dimension defines a dimension along the x-axis corresponding to a first height of the second needle end, the first height being less than a corresponding shaft height of the central shaft.

6. The surgical needle according to claim 5 wherein the first height is not greater than about 0.5 times the shaft height.

7. The surgical needle according to claim 1 wherein the needle body is curved along the longitudinal y axis.

8. The surgical needle according to claim 7 wherein the needle body defines an angle of curvature ranging from about 80° to about 180°.

9. The surgical needle according to claim 1 wherein the second needle end defines a maximum dimension along the z-axis greater than a corresponding maximum dimension along the z-axis of the central shaft.

10. A surgical needle, which comprises:
an elongated needle body defining a longitudinal y axis, the elongated needle body including a central shaft and having a first end for attachment to a suture and a second needle end for penetrating tissue, the second needle end having a transition area, a proximal portion of the second needle end disposed proximally of the transition area including a first length having a trapezoidal transverse cross-sectional dimension, and a distal portion of the second needle end disposed distally of the transition area including a second length having a triangular transverse cross-sectional dimension, the first length being longer than the second length, at least a portion of the first length having an area that decreases distally towards the second needle end, and at least a portion of the first length having an area that decreases proximally towards the central shaft of the needle body.

11. The surgical needle according to claim 10 wherein a maximum dimension of the second needle end is at least about 1.5 times a maximum dimension of the central shaft.

12. The surgical needle according to claim 10 wherein the trapezoidal cross-sectional dimension defines a dimension along a z-axes corresponding to a first width of the second needle end, the first width at least equal to a corresponding shaft width of the central shaft.

13. The surgical needle according to claim 12 wherein the first width is greater than a corresponding shaft width of the central shaft.

14. The surgical needle according to claim 13 wherein the first width is not less than about 1.5 times the shaft width.

15. The surgical needle according to claim 10 wherein the trapezoidal cross-sectional dimension defines a dimension along an x-axis corresponding to a first height of the second needle end, the first height being less than a corresponding shaft height of the central shaft.

16. The surgical needle according to claim 15 wherein the first height is not greater than about 0.5 times the shaft height.

17. The surgical needle according to claim 10 wherein the needle body is curved along the longitudinal y axis.

18. The surgical needle according to claim 17 wherein the needle body defines an angle of curvature ranging from about 80° to about 180°.

19. The surgical needle according to claim 10 wherein the second needle end defines a maximum dimension along a z-axis greater than a corresponding maximum dimension along the z-axis of the central shaft.

* * * * *